United States Patent [19]

Baer

[11] Patent Number: 4,517,130
[45] Date of Patent: May 14, 1985

[54] SUBSTITUTED AMINO ACID PROCESS

[75] Inventor: Ted A. Baer, Palo Alto, Calif.

[73] Assignee: Zoecon Corporation, Palo Alto, Calif.

[21] Appl. No.: 581,385

[22] Filed: Feb. 17, 1984

Related U.S. Application Data

[63] Continuation-in-part of Ser. No. 370,720, Apr. 22, 1982, abandoned.

[51] Int. Cl.$^3$ .................. C07C 121/78; C07C 101/447
[52] U.S. Cl. ............................ 260/465 E; 260/465 D; 549/439; 562/426; 562/433; 562/452; 562/453; 562/456
[58] Field of Search ...................... 260/465 E; 560/43; 562/433, 456, 426, 452, 453; 549/439

[56] References Cited

U.S. PATENT DOCUMENTS 4,226,802 10/1980 Anderson et al. .............. 260/465 E
4,243,819  1/1981 Henrick et al. ..................... 562/433

Primary Examiner—Dolph H. Torrence
Attorney, Agent, or Firm—Hana Dolezalova; Jacqueline S. Larson

[57] ABSTRACT

An improved process for preparing substituted amino acids and lower alkyl esters thereof, and intermediates therefor, comprising reacting a substituted aniline, HCN and an aldehyde to form a nitrile, converting the nitrile to an imidate salt with a strong acid and an alcohol, hydrolyzing in situ the imidate salt to the ester with addition of water, and optionally converting the ester to the salt or free acid. The acids are useful intermediates in the synthesis of pesticides.

17 Claims, No Drawings

SUBSTITUTED AMINO ACID PROCESS

RELATIONSHIP TO COPENDING APPLICATION

This application is a continuation-in-part of Ser. No. 370,720 filed Apr. 22, 1982, abandoned.

FIELD OF THE INVENTION

This invention relates to an improved process for the preparation of substituted amino acids and lower alkyl esters thereof, and intermediates therefor, which acids are useful in the synthesis of pesticides. More particularly, the acids of Formula I below are important intermediates in the synthesis of 3-phenoxybenzyl and α-cyano-3-phenoxybenzyl esters thereof, which esters are useful insecticides and acaricides as described by C. A. Henrick and B. A. Garcia in U.S. Pat. No. 4,243,819.

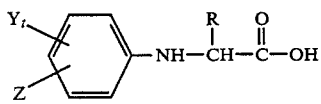  (I)

wherein, t is zero, one, two, three or four;

Y is independently selected from hydrogen, lower alkyl, lower haloalkyl, lower alkoxy, lower haloalkoxy, lower alkylthio, lower haloalkylthio, lower alkylcarbonyl, lower alkoxycarbonyl, and halogen;

Z is independently selected from the values of Y and cycloalkyl; or Y and Z together form a methylenedioxy group; and R is lower alkyl, lower alkenyl, cycloalkyl or hydrogen.

BACKGROUND OF THE INVENTION

Description of the Prior Art

The preparation of a particular acid of formula I, 2-(4-trifluoro-methylphenylamino)-3-methylbutanoate, and ortho-substituted derivatives thereof has been described in U.S. Pat. No. 4,226,802 to R. J. Anderson and T. A. Baer. In the Anderson et al process 4-aminobenzotrifluoride, or the corresponding ortho-substituted compound, is reacted with the sodium bisulfite addition product of isobutyraldehyde in an aqueous reaction medium, at a temperature above room temperature, followed by addition of sodium cyanide or potassium cyanide in aqueous medium to form the desired nitrile. The nitrile, on treatment with hydrochloric acid or other strong acid and an alcohol such as methanol at an elevated temperature forms a mixture of ester and amide. The ester can then be converted into the acid, or salt thereof.

Although the process of Anderson et al can be used to prepare other acids of Formula I as well, it is not satisfactory for commercial preparation of the acids of Formula I for several reasons. For example, in the preparation of the nitrile intermediate, solvents are required and a low yield (about 44%) of the nitrile is produced. Work-up is required before proceeding to the next step. In the preparation of the ester intermediate from the nitrile, the reaction must be run at elevated temperatures and proceeds through the amide intermediate, giving a mixture of ester and amide intermediates, requiring the extra step of either separating these two intermediates by chromatography (with a resulting low yield of about 47% of the ester) or the ester and amide mixture can be heated at about 80° C. for a prolonged period (about four days) to convert most of the remaining amide to ester. The latter procedure would not be suitable for compounds with certain aromatic substituents which would be degraded by the severe conditions. Overall yields for preparing ethyl 2-(2-chloro-4-trifluoromethylphenylamino)-3-methylbutanoate by the Anderson et al process, for example, is only about 38.3 percent. In contrast, by the process of this invention yields as high as 74.4 percent of 2-(2-chloro-4-trifluoromethylphenylamino)-3-methylbutanoate can be obtained.

U.S. Pat. No. 3,538,152 describes a procedure for preparing unsubstituted amino acid salts by reacting aniline, formaldehyde and hydrocyanic acid in an aqueous solution at an elevated temperature to form the nitrile. This is treated with an aqueous, alkaline solution at an elevated temperature, producing an amide intermediate which subsequently hydrolyzed directly to the salt. No ester intermediate is involved, and prolonged, severe conditions, which degrade a variety of aromatic substituents, are required to effect the amide hydrolysis.

SUMMARY OF THE INVENTION

In summary, the overall process of this invention yields a compound of the formula:

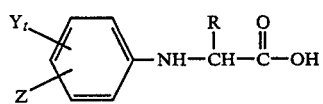  (I)

wherein, t is zero, one, two, three or four;

Y is independently selected from hydrogen, lower alkyl, lower haloalkyl, lower alkoxy, lower haloalkoxy, lower alkylthio, lower haloalkylthio, lower alkylcarbonyl, lower alkoxycarbonyl and halogen;

Z is independently selected from the values of Y and cycloalkyl; or Y and Z together form a methylenedioxy group; and R is lower alkyl, lower alkenyl, cycloalkyl or hydrogen.

The process comprises:

(a) reacting an amine of the formula (II):

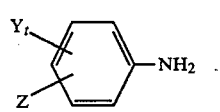  (II)

with at least one molar equivalent of hydrogen cyanide and at least one molar equivalent of an aldehyde of Formula III wherein the initial reaction mixture is initially substantially water-free and the water produced during the reaction does not exceed 7 weight percent of the reaction mixture,

  (III)

a nitrile of Formula IV is formed;

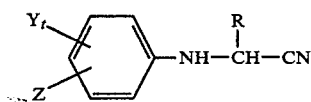

(b) a nitrile product of Formula IV is reacted with a strong acid in $R^1OH$, wherein $R^1$ is methyl or ethyl, to yield a non-aqueous solution of the imidate salt of Formula V,

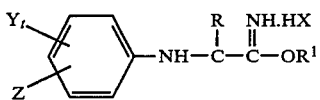

wherein X is anion of a strong mineral acid;

(c) water is added to the non-aqueous solution of the imidate salt to form an ester of the Formula VI, and

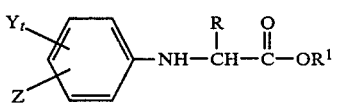

(d) finally the ester is reacted with sodium hydroxide in methanol or ethanol to form an acid of Formula I.

DETAILED DESCRIPTION OF THE INVENTION

The process of the present invention can be illustrated as follows:

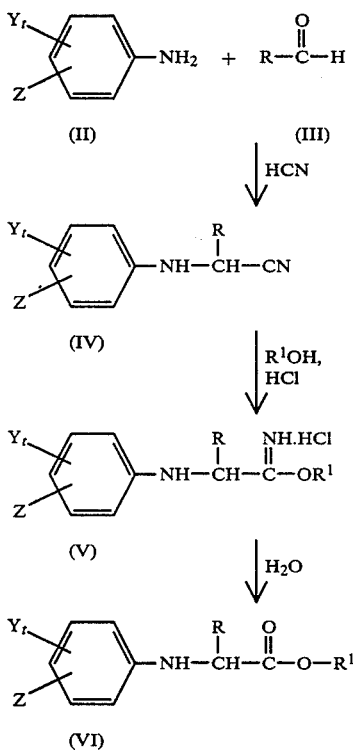

In the practice of the above-outlined synthesis, the amine of Formula II is reacted with at least one molar equivalent of hydrogen cyanide and with one molar equivalent of the aldehyde (III) at room temperature or below. This reaction is carried out neat, that is, without added solvent. The reaction mixture is initially water-free, i.e. contains less than one weight percent water, and the amount of water formed in the reaction mixture during the reaction does not exceed 7 weight percent of the reaction mixture. The resulting nitrile (IV) is treated with hydrochloric acid or other strong mineral acid to saturation in ethanol or methanol to form a non-aqueous solution of the imidate salt (V). To this solution is added water to form the ester (VI). The ester (VI) can be converted into the acid (I), or salt thereof, for use in preparing the pesticidally active 3-phenoxybenzyl esters.

The nitrile (IV) or the ester (VI) where R is hydrogen can be converted to the corresponding nitrile or ester, respectively, where R is lower alkyl or lower alkenyl by treatment with a base such as potassium t-butoxide and then with an alkyl (or alkenyl or cycloalkyl) halide such as isopropyl or 3-butenyl bromide.

In place of using an ortho substituted amine of Formula II, the ortho substituent can be introduced following formation of the nitrile (IV). For example, the nitrile (IV, Y is hydrogen) on reaction with a source of positive halogen, such as, for example, N-chlorosuccinimide or N-bromosuccinimide, in organic solvent gives the ortho substituted nitrile (IV, Y is chloro or bromo in this example) which is then converted to the ester as above.

The following terms, wherever used in the description herein and the appended claims, have the meaning defined below, unless otherwise specified hereinafter.

The term "lower alkyl" refers to an alkyl group, straight or branched, having a chain length of one to six carbon atoms. The term "lower haloalkyl" refers to an alkyl group substituted with one to three halogen atoms such as chloromethyl, fluoromethyl, and the like.

The term "lower alkoxy" refers to an alkoxy group, straight or branched, having a chain length of one to eight carbon atoms. The term "lower haloalkoxy" refers to an alkoxy group substituted with one to three halogen atoms.

The term "lower alkylthio" refers to an alkylthio group, straight or branched, having a chain length of one to eight carbon atoms. The term "lower haloalkylthio" refers to an alkylthio group substituted with one to three halogen atoms.

The term "cycloalkyl" refers to a cycloalkyl group of three to eight cyclic carbon atoms.

The term "lower alkenyl" refers to an ethylenically unsaturated hydrocarbon group, straight or branched, having a chain length of two to eight carbon atoms and one or two ethylenic bonds such as vinyl, allyl, 3-butenyl, 2-hexenyl, i-propenyl, 2,4-hexadienyl, and the like.

The following examples are provided to illustrate the practice of the present invention. Experiments which have been carried out are presented in the past tense. Hypothetical portions are presented in the present tense. Temperatures are given in degrees Centigrade.

EXAMPLE 1

To 17.7 g (110 mmol) of 4-amino-benzotrifluoride at 10° was added 3.5 g (130 mmol) of hydrogen cyanide. This solution was placed in a −15° dry ice-isopropyl alcohol bath. Pure isobutyraldehyde (7.9 g, 110 mmol) was added dropwise to the solution, maintaining a solution temperature of 15°–16°. The initial reaction mixture contained no water, and the water produced in the reaction did not exceed 6.8 wt. % of the reaction mixture. The ice bath was removed and the mixture was heated briefly to 48° and then allowed to cool to room temperature. The mixture was poured into ether, washed with 2.5N sodium hydroxide and then with water, dried over sodium sulfate, filtered and stripped to give the crude product, which upon recrystallization in ether/hexane yielded 3-methyl-2-(4-trifluoromethylphenylamino)butyronitrile, m.p. 64.5°–67°, 83% yield.

EXAMPLE 2

To a solution of 484 mg (2 mmol) of 3-methyl-2-(4-trifluoromethylphenylamino)butyronitrile in 5 ml of carbon tetrachloride was added 267 mg (2 mmol) of N-chlorosuccinimide. The mixture was heated at 65°. After about 48 hours, the mixture was poured into water and ether. The organic fraction was separated, washed with water and brine, dried over sodium sulfate, and solvent removed to give 3-methyl-2-(2-chloro-4-trifluoromethylphenylamino)butyronitrile in virtually quantitative yield.

EXAMPLE 3

To a solution of 3 g of 3-methyl-2-(2-chloro-4-trifluoromethylphenylamino)butyronitrile in 8 ml of ethanol was added gaseous HCl to saturation (4.4 g). The solution was stirred for 9 hours at room temperature, after which it was placed under 200 mm vacuum for 10 minutes to form a solution of the corresponding imidate hydrochloride. This solution was cooled to 15°–19°, and 10 ml of water was added. This mixture was stirred at 22° for about 40 hours. It was then worked up by adding water and ether and separating the organic layer. This was washed with water, dried and the solvent removed to yield the ester, ethyl 2-(2-chloro-4-trifluoromethylphenylamino)-3-methylbutanoate, 93% yield.

To 0.60 grams of sodium hydroxide dissolved in 10 ml of ethanol was added 3.30 g of the above ester. The mixture was stirred at room temperature for 4 hours, after which water was added, and the mixture was washed with toluene. The organic phase was discarded. The product was acidified, extracted into ether, washed with water, dried and solvent removed to yield 2-(2-chloro-4-trifluoromethylphenylamino)-3-methylbutanoic acid, m.p. 132°–135°, in 90% yield.

EXAMPLE 4

Following the procedure of Example 1, each of 3-chloro-4-aminobenzotrifluoride and 3-fluoro-4-aminobenzotrifluoride is reacted with hydrogen cyanide and isobutyraldehyde, in a neat, initially water-free system, to give the respective nitrile, 2-(2-chloro-4-trifluoro-methylphenylamino)-3-methylbutyronitrile and 2-(2-fluoro-4-trifluoromethylphenylamino)-3-methylbutyronitrile.

EXAMPLE 5

Following the procedure of Example 3, 2-(4-trifluoromethylphenylamino)-3-methylbutyronitrile was treated, at room temperature, with ethanol/HCl and then, at slightly lower temperature, with water to give ethyl 2-(4-trifluoromethylphenylamino)-3-methylbutanoate.

In the same way, ethyl 2-(2-fluoro-4-trifluoromethylphenylamino)-3-methylbutanoate is made from 2-(2-fluoro-4-trifluoromethylphenylamino)-3-methylbutyronitrile.

EXAMPLE 6

Following the procedure of Example 1, each of the amines in column I is reacted with isobutyraldehyde in the presence of hydrogen cyanide in a neat, initially water-free system to give the corresponding nitrile in column II.

I aniline
4-methylthioaniline
2,3,4,5-tetrafluoroaniline
4-chloro-2-fluoroaniline
6-chloro-2-fluoro-4-trifluoromethylaniline
4-chloroaniline
4-methoxyaniline
4-difluoromethoxyaniline

II 3-methyl-2-phenylaminobutyronitrile
3-methyl-2-(4-methylthiophenylamino)butyronitrile
3-methyl-2-(2,3,4,5-tetrafluorophenylamino)-butyronitrile
3-methyl-2-(4-chloro-2-fluorophenylamino)butyronitrile
3-methyl-2-(6-chloro-2-fluoro-4-trifluoromethylphenylamino)butyronitrile
3-methyl-2-(4-chlorophenylamino)butyronitrile
3-methyl-2-(4-methoxyphenylamino)butyronitrile
3-methyl-2-(4-difluormethoxyphenylamino)butyronitrile Using the method of Example 3, the nitriles of column II are treated with ethanol/HCl and then with water to give the corresponding butanoic acid esters of column III.

III ethyl 2-phenylamino-3-methylbutanoate
ethyl 2-(4-methylthiophenylamino)-3-methylbutanoate
ethyl 2-(2,3,4,5-tetrafluorophenylamino)-3-methylbutanoate
ethyl 2-(4-chloro-2-fluorophenylamino)-3-methylbutanoate
ethyl 2-(6-chloro-2-fluoro-4-trifluoromethylphenylamino)methylbutanoate
ethyl 2-(4-chlorophenylamino)-3-methylbutanoate
ethyl 2-(4-methoxyphenylamino)-3-methylbutanoate
ethyl 2-(4-difluoromethoxyphenylamino)-3-methylbutanoate

EXAMPLE 7

3-Chloro-4-aminobenzotrifluoride and hydrogen cyanide are reacted with each of acetaldehyde, 2-propenal, 3-butenal, and cyclopropylcarboxyaldehyde, in a neat, initially water-free system following the procedure of Example 1, to yield
2-(2-chloro-4-trifluoromethylphenylamino)ethylnitrile,
2-(2-chloro-4-trifluoromethylphenylamino)propylnitrile,
2-(2-chloro-4-trifluoromethylphenylamino)-4-pentenylnitrile, and
2-(2-chloro-4-trifluoromethylphenylamino)-2-cyclopropylethylnitrile.

Each of the above nitriles is then reacted with ethanol/HCl and then with water, as in Example 3, giving ethyl 2-(2-chloro-4-trifluoromethylphenylamino)ethanoate,
ethyl 2-(2-chloro-4-trifluoromethylphenylamino)propanoate,
ethyl 2-(2-chloro-4-trifluoromethylphenylamino)-4-pentenoate, and
ethyl 2-(2-chloro-4-trifluoromethylphenylamino)-2-cyclopropylethanoate.

EXAMPLE 8

Following the procedure of Example 3, each of the esters in column IV below is reacted with sodium hydroxide in ethanol, after which water is added to yield the carboxylic acids under column V.

IV ethyl 2-phenylamino-3-methylbutanoate
ethyl 2-(4-trifluoromethylphenylamino)-3-methylbutanoate
ethyl 2-(6-chloro-2-fluoro-4-trifluoromethylphenylamino)-3-methylbutanoate
ethyl 2-(4-methoxyphenylamino)-3-methyl-butanoate
ethyl 2-(4-chloro-2-methylphenylamino)-3-methylbutanoate
ethyl 2-(2-fluoro-4-trifluoromethylphenylamino)-3-methylbutanoate
ethyl 2-(2-chloro-4-trifluoromethylphenylamino)propanoate
ethyl 2-(2-chloro-4-trifluoromethylphenylamino)-3-butenoate
ethyl 2-(2-chloro-4-trifluoromethylphenylamino)-2-cyclopropylethanoate.

V 2-phenylamino-3-methylbutanoic acid
2-(4-trifluoromethylphenylamino)-3-methylbutanoic acid
2-(6-chloro-2-fluoro-4-trifluoromethylphenylamino)-3-methylbutanoic acid
2-(4-methoxyphenylamino)-3-methylbutanoic acid
2-(4-chloro-2-methylphenylamino)-3-methylbutanoic acid
2-(2-fluoro-4-trifluoromethylphenylamino)-3-methylbutanoic acid
2-(2-chloro-4-trifluoromethylphenylamino)propanoic acid
2-(2-chloro-4-trifluoromethylphenylamino)-3-butenoic acid
2-(2-chloro-4-trifluoromethylphenylamino)-2-cyclopropylethanoic acid

What is claimed is:

1. A process for the preparation of a compound of formula (IV):

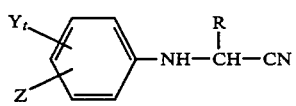 (IV)

wherein,
t is zero, one, two, three or four;
Y is independently selected from hydrogen, lower alkyl, lower haloalkyl, lower alkoxy, lower haloalkoxy, lower alkylthio, lower haloalkylthio, lower alkylcarbonyl, lower alkoxycarbonyl and halogen;
Z is independently selected from the values of Y and cycloalkyl, or Y and Z together form a methylenedioxy group; and
R is lower alkyl, lower alkenyl, cycloalkyl or hydrogen;
which comprises the step of reacting a compound of formula (II):

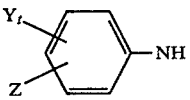 (II)

with hydrogen cyanide and an aldehyde

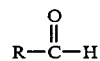 (III)

wherein the reaction is carried out in an initially, substantially water-free reaction mixture, and the water produced in the reaction does not exceed 7 wt. % of the reaction mixture.

2. A process for the preparation of a compound of the formula (V):

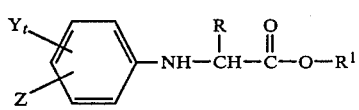 (V)

wherein,
t is zero, one, two, three or four;
Y is independently selected from hydrogen, lower alkyl, lower haloalkyl, lower alkoxy, lower haloalkoxy, lower alkylthio, lower haloalkylthio, lower alkylcarbonyl, lower alkoxycarbonyl and halogen;
Z is independently selected from the values of Y and cycloalkyl; or Y and Z together form a methylenedioxy group;
R is lower alkyl, lower alkenyl, cycloalkyl or hydrogen; and
$R^1$ is methyl or ethyl;
which comprises:
(a) reacting a compound of formula (IV):

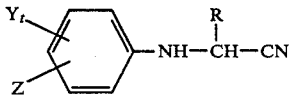 (IV)

wherein,
t is zero, one, two, three or four;
Y is independently selected from hydrogen, lower alkyl, lower haloalkyl, lower alkoxy, lower haloalkoxy, lower alkylthio, lower haloalkylthio, lower alkylcarbonyl, lower alkoxycarbonyl and halogen;
Z is independently selected from the values of Y and cycloalkyl, or Y and Z together form a methylenedioxy group; and
R is lower alkyl, lower alkenyl, cycloalkyl or hydrogen; with an alcohol $R^1$—OH and strong acid to form a non-aqueous solution of the imidate salt of formula (V):

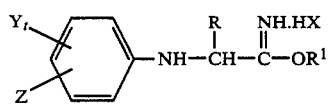
(V)

wherein X is the anion of a strong mineral acid, and (b) adding water to the non-aqueous solution of the imidate salt.

3. A process as claimed in claim 2 wherein the reaction is carried out at room temperature or below.

4. A process as claimed in claim 3 wherein the strong acid is hydrochloric acid.

5. A process as claimed in claim 4 wherein $R^1$ is ethyl.

6. A process for preparing a compound of formula (I):

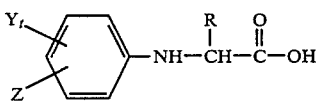
(I)

wherein, t is zero, one, two, three or four;

Y is independently selected from hydrogen, lower alkyl, lower haloalkyl, lower alkoxy, lower haloalkoxy, lower alkylthio, lower haloalkylthio, lower alkylcarbonyl, lower alkoxycarbonyl, and halogen;

Z is independently selected from the values of Y and cycloalkyl; or Y and Z together form a methylenedioxy group; and R is lower alkyl, lower alkenyl, cycloalkyl or hydrogen;

which comprises:

(a) reacting an amine of formula (II):

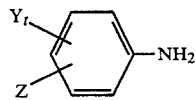
(II)

with at least one molar equivalent of hydrogen cyanide and at least one molar equivalent of an aldehyde of the formula

(III)

to form a nitrile of formula (IV):

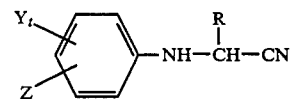
(IV)

(b) reacting a nitrile of formula (IV) with a strong acid in $R^1OH$, wherein $R^1$ is methyl or ethyl, to yield a non-aqueous solution of the imidate salt of formula (V):

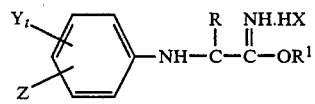
(V)

wherein X is the anion of a strong mineral acid, (c) adding water to the non-aqueous solution of an imidate of formula (IV) to form an ester of formula (VI):

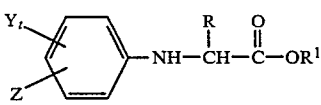
(VI)

and, (d) reacting said ester with sodium hydroxide in methanol or ethanol and acidifying it to form an acid of formula (I).

7. The process according to claim 6 wherein the reaction of step (a) is carried out neat.

8. The process of claim 7 wherein step (b) is carried out at room temperature or below.

9. The process of claim 8 wherein the strong acid is gaseous HCl in ethanol or methanol.

10. The process of claim 9 wherein R is isopropyl, t is zero, and Z is trifluoromethyl in the para position.

11. The process of claim 1 wherein t is zero or one, Z is trifluoromethyl in the para position, and R is isopropyl.

12. The process of claim 11 wherein t is zero.

13. The process of claim 11 wherein t is one and Y is chloro in the ortho position.

14. The process of claim 3 wherein t is zero or one, Z is trifluoromethyl in the para position, and R is isopropyl.

15. The process of claim 14 wherein t is zero.

16. The process of claim 14 wherein t is one and Y is chloro in the ortho position.

17. The process of claim 9 wherein t is one and Y is chloro in the ortho position, Z is trifluoromethyl in the para position, and R is isopropyl.

* * * * *